United States Patent [19]

Meguro et al.

[11] Patent Number: 4,596,816
[45] Date of Patent: Jun. 24, 1986

[54] 4-ARYL OXAZOLES

[75] Inventors: Kanji Meguro; Takeshi Fujita, both of Hyogo, Japan

[73] Assignee: Takeda Chemical Industries, Ltd., Osaka, Japan

[21] Appl. No.: 485,433

[22] Filed: Apr. 15, 1983

[30] Foreign Application Priority Data

Apr. 19, 1982 [JP] Japan ............................. 57-66124

[51] Int. Cl.⁴ .................... C07D 263/32; A61K 31/42
[52] U.S. Cl. .................................... 514/374; 548/236
[58] Field of Search ................. 548/236; 424/272; 514/374

[56] References Cited

U.S. PATENT DOCUMENTS 3,578,671  5/1971  Brown ............................ 548/236
3,579,529  5/1971  Brown ............................ 548/236

Primary Examiner—George F. Lesmes
Assistant Examiner—S. A. Gibson
Attorney, Agent, or Firm—Cohen, Pontani & Lieberman

[57] ABSTRACT

Novel oxazole derivatives of the formula

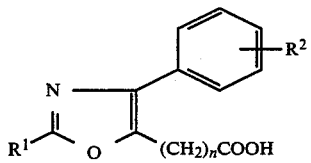

(wherein $R^1$ is hydrogen or a straight, branched or cyclic alkyl group of 1 to 6 carbon atoms, $R^2$ is hydrogen, halogen, trifluoromethyl, or a straight, branched or cyclic alkylthio of 1 to 3 carbon atoms, and n is 1 or 2) or pharmaceutically acceptable salts or esters thereof are synthesized through several routes. The derivatives have hypoglycemic, glucose tolerance improving and insulin sensitivity increasing activities and are of value as antidiabetic drugs.

19 Claims, No Drawings

4-ARYL OXAZOLES

This invention relates to novel oxazole derivatives which are of value as medicines.

More particularly, this invention relates to an oxazole derivative of the formula

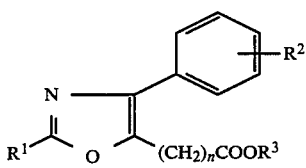
(I)

wherein $R^1$ is a hydrogen atom or a lower alkyl group; $R^2$ is a hydrogen atom, a halogen atom, a trifluoromethyl group or a lower alkylthio group; $R^3$ is a hydrogen atom or a lower alkyl group; n is 1 or 2 or a salt thereof.

The research undertaken to develop new oxazole derivatives (I) led the present inventors to the finding that the compound represented by the above general formula displays certain desirable activities such as hypoglycemic activity, glucose tolerance improving activity, insulin sensitivity increasing activity, etc. in mammalian animals and is of value as an antidiabetic drug. This invention is predicated on the above finding.

Referring to the above general formula (I), the lower alkyl groups $R^1$ and $R^3$ include straight-chain, branched and cyclic alkyl groups each containing 1 to 6 carbon atoms, such as methyl, ethyl, propyl, isopropyl, butyl, isobutyl, sec-butyl, tert-butyl, pentyl, isopentyl, neopentyl, hexyl, cyclopropylmethyl, cyclopentyl, cyclohexyl, etc. Preferred examples of $R^1$ are straight-chain alkyl groups of 1 to 3 carbon atoms, and those of $R^3$ are straight-chain or branched alkyl groups of 1 to 4 carbon atoms.

The substituent $R^2$ may be present in any position of the benzene ring, and the halogen as an example of $R^2$ may be florine, chlorine, bromine or iodine, preferably, fluorine or chlorine. The lower alkylthio group for $R^2$ may be a straight, branched or cyclic containing 1 to 3 carbon atoms, such as methylthio, ethylthio, etc. The object compound (I) of this invention can be produced by any of the following processes.

(1)

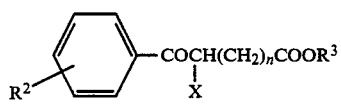
(II)

wherein X is a halogen atom (e.g. Cl, Br); other symbols are as defined above, is reacted with a compound of formula (III)

$$R^1CONH_2 \quad (III)$$

wherein $R^1$ is as defined above, to give the object compound (I).

The reaction of (II) with (III) is generally conducted by heating a mixture of (II) and (III) at a temperature of about 50° to 200° C., preferably about 80° to 160° C., in the absence of a solvent. The molar proportion of compound (III) relative to each mole of (II) is 1 to 20 moles and preferably 5 to 12 moles. To accept the byproduct hydrogen halide (HX), there may be added a base (e.g. sodium carbonate, potassium carbonate, calcium carbonate) to the reaction system in a molar proportion of 1 to 5 moles per mole of (II). When the reaction product (I) is an ester, it may be hydrolyzed to the corresponding carboxylic acid. This hydrolysis reaction is preferably conducted using an alkali (e.g. sodium hydroxide, potassium hydroxide) in the presence of a solvent (e.g. water, methanol, ethanol, propanol) at a temperature of about 0° to 150° C. and preferably at about 20° to 100° C. The molar proportion of the alkali relative to (I) is about 1 to 5 equivalents, preferably about 2 to 4 equivalents.

When the compound (I) is a carboxylic acid, it may be esterified to a desired ester. This esterification reaction may be carried out by the conventional procedure, for example by reacting (I) with an alkylating agent such as diazomethane, an alkyl halide, an alkyl sulfate ester, an alkyl sulfonate ester or the like, if necessary in the presence of a base such as sodium carbonate, potassium carbonate, sodium hydride, etc., or by a process which involves the use of thionyl chloride and alkanol, or by a process in which a mixed acid anhydride is prepared and esterified with an alkanol, or by a process involving the use of an anhydrous mineral acid (e.g. sulfuric acid, hydrogen chloride, hydrogen bromide) and an alkanol.

(2) The object compound (I) wherein n=2 can also be produced by the following route, for instance. A compound of the formula

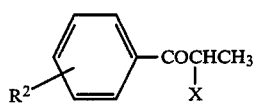
(IV)

wherein all symbols are as defined above, is reacted with a compound of formula (III) to give a compound of the formula

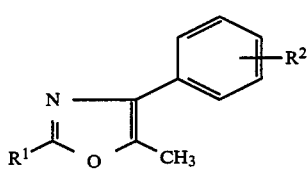
(V)

wherein $R^1$ and $R^2$ are as defined above, which is then halogenated to give a compound of the formula

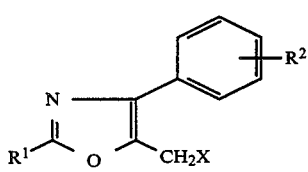
(VI)

wherein all symbols are as defined above. This compound (VI) is then reacted with a malonic acid derivative of the formula $$CH_2(COOR^4)_2 \quad (VII)$$

wherein $R^4$ is a straight, branched or cyclic alkyl group of 1 to 6 carbon atoms, to give a compound of the formula

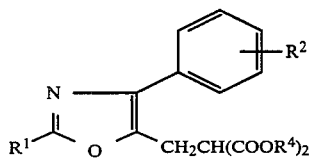 (VIII)

wherein all symbols are as defined above. The compound (VIII) is then hydrolyzed and decarboxylated to a compound of the formula

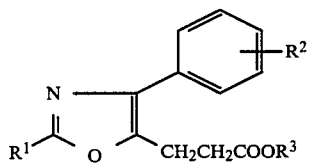 (IX)

wherein all symbols are as defined above.

Referring to the above formulas, the lower alkyl group $R^4$ may be one of those mentioned for $R^3$.

The reaction of compound (IV) with compound (III) may be conducted in exactly the same manner as the reaction of compound (II) with (III). The halogenation reaction of (V) to give (VI) can be generally conducted with advantage using an N-haloacetamide or an N-halosuccinimide in an inert solvent (e.g. carbon tetrachloride, chloroform, dichloromethane). It is particularly advantageous to employ an N-halosuccinimide and, especially, N-bromosuccinimide. This reaction proceeds more smoothly in the presence of a radical initiator such as azobisisobutyronitrile, benzoyl peroxide or the like. The molar proportion of such a N-haloimide relative to compound (V) is generally 1 to 1.2 equivalents, while the proportion of said radical initiator relative to (V) is a catalytic amount, e.g. about 0.01 to 0.2 equivalent. The reaction proceeds smoothly in the temperature range of room temperature to the boiling point of the solvent.

Then, compound (VI) is reacted with (VII) to give (VIII). This reaction is generally conducted in the presence of a base and preferably in an appropriate solvent. The base mentioned just above may for example be an alkoxide (e.g. methoxide, ethoxide, propoxide, t-butoxide), amide or hydride of sodium or potassium, and the solvent may for example be an alkanol (e.g. methanol, ethanol, propanol, isopropyl alcohol), and ether (e.g. dimethoxyethane, tetrahydrofuran, dioxane), N,N-dimethylformamide or dimethyl sulfoxide. This reaction is generally conducted at a temperature of $-30°$ C. to $+40°$ C., although it may be carried out at a lower or higher temperature, if desired.

The compound (VIII) is then hydrolyzed and decarboxylated to compound (IX). This reaction may be carried out either in a single step, i.e. by subjecting (VIII) to concurrent hydrolysis and decarboxylation with a mineral acid (e.g. hydrochloric acid, hydrobromic acid) to give (IX) wherein $R^3$ is a hydrogen atom or by a serial step, i.e. by hydrolyzing the ester moiety with an alkali (e.g. sodium hydroxide, potassium hydroxide) in an alkanol such as methanol at a temperature from room temperature to the boiling point of the solvent, and then, decarboxylating the hydrolysis product under heating to give (IX). The decarboxylation can be carried out by heating the hydrolysis product at a temperature of about 60° to 150° C. in a solvent such as an alkanol, pyridine, dimethylformamide, dimethylsufoxide, etc., which may be accelerated by the addition of a mineral acid. If, in the latter process, 1 to 1.2 moles of the alkali is used per mole of (VIII), only one of the ester bonds is hydrolyzed so that decarboxylation gives (IX) in which $R^3$ is the same ester residue as $R^4$, but if 2 molar equivalents or more of the alkali is employed, both of the ester bonds of (VIII) are hydrolyzed so that decarboxylation gives (IX) in which $R^3$ is a hydrogen atom. To convert (VIII) to (IX) wherein $R^3$ is a hydrogen atom in a single step, a suitable solvent may be employed to dissolve (VIII) and (IX). Examples of the solvent include ethanol, propanol, isopropyl alcohol, butanol, acetic acid, etc. and the reaction temperature is preferably 70° to 150° C.

(3) In process (2), instead of producing (V) from (IV) and (III), (V) can also be produced by the following procedures. Thus, a compound of formula (X)

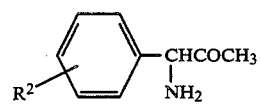 (X)

wherein $R^2$ is as defined above, is reacted with a carboxylic acid of formula (XI)

$R^1COOH$ (XI)

wherein $R^1$ is as defined above, or a reactive derivative thereof to give a compound of formula (XII)

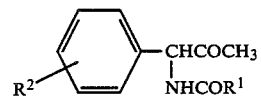 (XII)

wherein $R^1$ and $R^2$ are as defined above, which is then cyclized with the elimination of water to give a compound of formula (V).

The reaction of compounds (X) and (XI) to give (XII) may be carried out by a per se known process, e.g. one using dicyclohexylcarbodiimide or a mixed acid anhydride, for instance. Aside from such processes, (XII) can also be produced by a per se known process using a reactive derivative of (XI), e.g. the acid anhydride or an acid halide or active ester of (XI). This reaction may be carried out in a solvent, for example, benzene, toluene, chloroform, ethyl acetate, pyridine, etc., usually at a temperature from about 0° to 100° C. When an acid halide is used as the reactive derivative, a base, for example, pyridine, triethylamine, $Na_2CO_3$, $NaHCO_3$, etc., may be added to the reaction mixture. To produce the compound (V) by way of dehydrative cyclization of (XII), it is preferable to employ a suitable dehydrating agent (e.g. phosphorus oxychloride, thionyl chloride, phosphorus trichloride, phosphorus pentachloride, sulfuric acid, phosphorus pentoxide, polyphosphoric acid, polyphosphoric acid esters, etc.). This reaction can be advantageously conducted by using the above dehydrating agent also as the solvent and heating the reaction system at a temperature of 50° to 180° C. If necessary, a suitable inert solvent (e.g. chloroform, dichloromethane, benzene, toluene, xylene) may be employed. The proportion of the dehydrating agent is 1 to 10 moles, preferably 3 to 5 moles, per mole of (XII).

(4) The object compound (I) wherein n=7 can also be produced by the following procedures. A compound of formula (XIII)

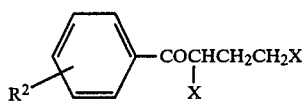

wherein $R^2$ and X are as defined above, is reacted with a compound of formula (III) to give a compound of formula (XIV)

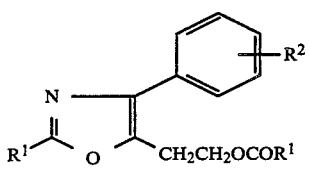

wherein all symbols are as defined above, which is then hydrolyzed to a compound of formula (XV)

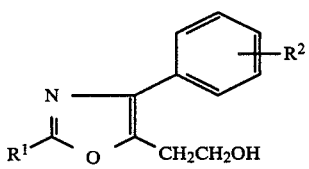

wherein $R^1$ and $R^2$ are as defined above, which is further halogenated to give a compound of formula (XVI)

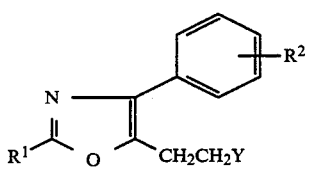

wherein $R^1$ and $R^2$ are as defined above; and Y is a chlorine, bromine or iodine atom. This compound (XVI) is reacted with sodium cyanide or potassium cyanide to give a compound of formula (XVII)

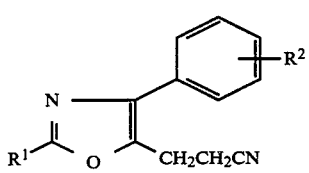

wherein $R^1$ and $R^2$ are as defined above, which is then hydrolyzed and, if necessary, esterified to give compound (I).

In this process, reacting (XIII) with amide (III) in exactly the same manner as the above reaction of (II) with (III) gives a compound (XIV) by way of the formation of an oxazole ring and replacement of one of the halogen atoms with an ester group. The compound (XIV), on hydrolysis under the same conditions as hydrolysis of the ester group of (I), gives an alcohol (XV). This alcohol is then halogenated to (XVI). This halogenation reaction is conducted using, for instance, thionyl chloride or phosphorus tribromide in a solvent such as chloroform, dichloromethane, etc. and, if necessary, in the presence of N,N-dimethylformamide at a temperature of $-10°$ C. to $+70°$ C., whereby a compound (XVI) in which Y is a chlorine atom or a bromine atom is obtained. These compounds may be converted to (XVI) wherein Y is an iodine atom by treating them with sodium iodide or potassium iodide in a solvent such as acetone, methyl ethyl ketone or the like under reflux conditions. Of these compounds (XVI), the compound in which Y is an iodine atom is the most reactive and, therefore, especially desirable. The compound (XVI) is then cyanized to give (XVII). This reaction is accomplished by treating (XVI) with sodium cyanide or potassium cyanide in a suitable solvent. Examples of the solvent include alkanols such as methanol, ethanol, etc., N,N-dimethylformamide, dimethyl sulfoxide, etc., although dimethyl sulfoxide is preferred. The reaction is generally conducted in the neighborhood of room temperature but it may be conducted at an elevated temperature. The compound (XVII) is then hydrolyzed and, if necessary, esterified to give the object compound (I). This hydrolysis reaction can be advantageously conducted using an alkali such as sodium hydroxide or potassium hydroxide to give the carboxylic acid (I). The molar proportion of said alkali is generally 1 to 6 equivalents and preferably 2 to 5 equivalents per mole of (XVII), and the reaction temperature is generally the boiling point of the solvent used or thereabouts. The solvent is preferably an aqueous alkanol such as aqueous methanol, ethanol, propanol, butanol or 2-methoxyethanol.

(5) The object compound (I) wherein n=2 can also be produced by the following procedure. Namely, a compound of the formula (VI)

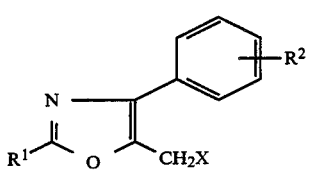

wherein all symbols are as defined above, described in the above-mentioned procedure (2), is reacted with an α-haloacetoacetic ester of the formula (XVIII)

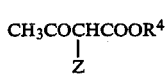

wherein Z is a halogen atom and $R_4$ is as defined above to produce a compound of the formula (XIX)

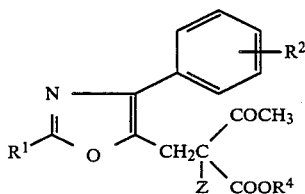

(XIX)

wherein all symbols are as defined above), which is then subjected to deacetylation reaction to produce a compound of the formula (XX)

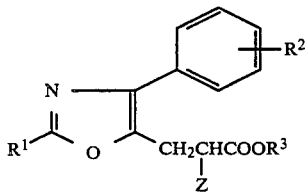

(XX)

wherein all symbols are as defined above, and further the compound of the formula (XX) is subjected to dehalogenation reaction to produce a compound of the formula (IX)

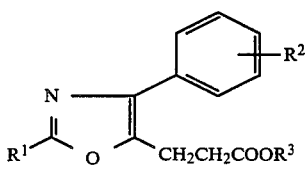

(IX)

wherein all symbols are as defined above.

The halogen denoted by Z in the above formulas means the same halogen as X aforementioned.

When compound (VI) is reacted with compound (XVIII) to produce compound (XIX), X and Z may be the same or different each other, however, the combination wherein X is bromine and Z is chlorine is most preferable. The reaction can be carried out under the same condition as the reaction of compounds (VI) with (VII) in the aforementioned process (2).

And then, compound (XIX) is subjected to deacetylation reaction to produce compound (XX). This reaction proceeds advantageously in a suitable solvent, usually in the presence of an alkali.

As the alkali, there may suitably be employed sodium hydroxide, potassium hydroxide, barium hydroxide, etc., and as the solvent, an alkanol such as methanol, ethanol, propanol, etc. The reaction temperature is usually from 0° to 100° C. When this reaction is carried out in the presence of water using not less than 2 equivalents of alkali, the ester bond is hydrolized together with the deacetylation to yield compound (XX) wherein $R^3$ is hydrogen. When the reaction is carried out under anhydrous condition, especially under addition of anhydrous barium hydroxide, compound (XX) wherein $R^3$ is a lower alkyl group is obtained. In these reactions, the amount of alkali employed is usually 1 to 5 moles per 1 mole of (XIX).

Compound (XX) thus obtained is further subjected to dehalogenation reaction to produce the object compound (IX). This reaction advantageously proceeds usually in the presence of a reducing agent. As the reducing agent, there may be exemplified hydrogen, or the combination of a metal and an acid. When hydrogen is employed, it is preferable to carry out catalytic reduction in the presence of suitable catalyst (e.g. palladium-carbon, palladium black, etc.) and a solvent (e.g. methanol, ethanol, propanol, ethyl acetate, etc.). This reaction may be carried out in the coexistence of an agent, for example, sodium acetate, potassium acetate or the aqueous solution thereof to remove hydrogen halide formed by the reaction. When a metal and an acid is employed, there may be exemplified zinc, iron, tin, etc. as the metal, and formic acid, acetic acid, hydrochloric acid, etc. as the acid. The acid may serve both as a reagent and a solvent. An alkanol such as methanol, ethanol, etc. may further be added as a solvent. The reaction temperature is usually from 20° to 100° C.

When the compound (I) obtained by any of the above processes (1) to (5) is a free carboxylic acid ($R^3$=H), it can be converted to a pharmaceutically acceptable salt with a base in the per se conventional manner. Examples of the salt include the sodium, potassium, aluminum and calcium salts.

The compound (I) and its salt according to this invention are novel compounds which have not been described in the literature to this day, and because these compounds display hypoglycemic activity, glucose tolerance improving activity, insulin sensitivity increasing activity, etc. in mammalian animals (e.g. mouse, rat, rabbit, dog, monkey, man) and, moreover, are only sparingly toxic, they are of value as antidiabetic drugs. For medical use, the compound (I) or a salt thereof may be formulated with a pharmaceutically acceptable carrier, excipient or diluent to prepare such dosage forms as powders, granules, tablets, capsules, injections, etc. and can be safely administered orally or otherwise. The dosage of (I) for diabetes depend on severity of the disease and other factors. Generally, the oral daily dosage for an adult human is about 1 to 30 mg per kg body weight, preferably about 2 to 20 mg, and is preferably administered in 2 to 3 divided doses.

Some pharmacological data showing the utility of compounds of this invention are presented below.

1. Insulin sensitivity increasing activity (in mice)

Bioassay: An insulin sensitivity test was carried out using male ICR mice, aged 7 to 9 weeks, which had been raised on CE-2 solid feed (Japan Clea, K.K.). Each of the ICR mice (in groups of 5 individuals) was dosed with 100 mg/kg of each test compound (as a suspension in 5% gum arabic solution) by oral route, and after fasting overnight (20 hours), dosed again with 100 mg/kg of the compound. Animals in a control group received a 5% aqueous solution of gum arabic. Thirty minutes after the second administration, 0.1 U/kg of insulin (Regular, Novo) was intraperitoneally injected. At 0, 60, 120 minutes after the injection, blood samples were taken from the orbital venous plexus to measure blood glucose levels. The measurement of glucose levels was made by an enzymatic technique using glucose oxidase. The relative strength of activity of each test compound was evaluated against the average glucose level of the control group and was shown as a percent (%) decrease in blood glucose.

Results: The test results are shown in Table 1.

TABLE 1

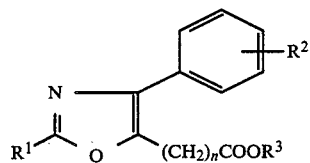

| No. | R¹ | R² | R³ | n | Insulin sensitivity test % Decrease in blood glucose | | |
|---|---|---|---|---|---|---|---|
| | | | | | 0 min. | 60 min. | 120 min. |
| 1 | CH₃ | H | H | 2 | 25 | 28 | 22 |
| 2 | CH₃ | p-Cl | H | 2 | 35 | 19 | 9 |
| 3 | CH₃ | p-Cl | H | 1 | −4 | 16 | 21 |
| 4 | CH₃ | m-Cl | H | 2 | 14 | 23 | 10 |
| 5 | CH₃ | p-F | H | 2 | 6 | 8 | 15 |
| 6 | CH₃ | m-CF₃ | H | 2 | −3 | 10 | 18 |
| 7 | CH₃ | p-CF₃ | H | 2 | 7 | 18 | 17 |

2. Hypoglycemic activity

Procedure: Using fasted male or female KKA$^y$ mice, which are genetically obese and diabetic, (10 to 13 weeks old, 5 animals per group), the hypoglycemic activity of a test compound was investigated. Thus, each KKA$^y$ mouse was fasted for 18 to 20 hours and, then, dosed with a suspension of 4-(4-chlorophenyl)-2-methyloxazole-5-propionic acid in 5% gum arabic solution by oral route. At 0, 60 and 120 minutes after the treatment, blood samples were taken from the orbital venous pexus to measure the blood glucose levels. The measurement of blood glucose was made by the glucose oxidase method.

Results: As apparent from Table 2, the activity of the test compound in lowering the blood glucose levels in fasted KKA$^y$ mice was dose-dependent and lasted for more than 120 minutes.

TABLE 2

| | Dosage (mg/kg, PO) | Blood glucose (mg/dl) | | |
|---|---|---|---|---|
| | | 0 min. | 60 min. | 120 min. |
| Control group | — | 175 ± 10 | 188 ± 33 | 161 ± 30 |
| Test group | 10 | 176 ± 30 | 169 ± 29 | 137 ± 20 |
| | 20 | 173 ± 31 | 144 ± 37 | 128 ± 28 |
| | 50 | 172 ± 32 | 128 ± 40 | 110 ± 34 |

3. Glucose tolerance improving activity

Procedure: The glucose tolerance improving activity of a compound of this invention was investigated in fatty rats with hereditary obesity showing reduced glucose tolerance (9 to 10 weeks old, 5 animals per group). Each fatty rat was fasted for 20 hours and, then, dosed with 100 mg/kg of 4-(4-chlorophenyl)-2-methyloxazole-5-propionic acid (as a suspension in 5% gum arabic solution) by oral route. After 90 minutes, the rat was orally loaded with 2 g/kg of glucose. At 0, 30, 60, 120 and 180 minutes after glucose loading, blood samples were taken from the caudal vein to measure the blood glucose and plasma insulin levels.

Results: Blood glucose was decreased significantly as compared with the control group. Thus, the blood glucose levels at 30, 60, 90 and 120 minutes after glucose loading were 61, 62, 64 and 74%, respectively, of the respective control levels. In blood insulin level, there was no significant difference between the test group and the control group.

The following working and preparation examples are further illustrative but by no means limitative of this invention.

EXAMPLE 1

(1) A mixture of α-bromopropiophenone (9.5 g) and acetamide (26.4 g) was heated on an oil bath at 130°–140° C. for 40 minutes. After cooling, saturated aqueous sodium hydrogen carbonate was added and the mixture was extracted with ethyl ether. The ether layer was washed with water and dried over anhydrous magnesium sulfate. The solvent was then distilled off and the residue was further distilled under reduced pressure to give 2,5-dimethyl-4-phenyloxazole as an oil, yield 6.4 g (82.9%), b.p. 148°–152° C./23 mmHg.

(2) A mixture of 2,5-dimethyl-4-phenyloxazole (6.0 g), N-bromosuccinimide (6.6 g), azobisisobutyronitrile (0.3 g) and carbon tetrachloride (120 ml) was refluxed with stirring for 5 minutes. The reaction mixture was washed with water, saturated aqueous sodium hydrogen carbonate and water in that order, and dried over anhydrous magnesium sulfate. The solvent was then distilled off and the oily residue was left standing to give 5-bromomethyl-2-methyl-4-phenyloxazole as crystals, yield 9.2 g (98.9%). Recrystallization from ethanol gave colorless needles, m.p. 80°–81° C.

Elemental analysis: Calcd. for $C_{11}H_{10}BrNO$: C, 52.41; H, 4.00; N, 5.56; Found: C, 52.57; H, 4.02; N, 5.71.

(3) 60% Sodium hydride in oil (1.48 g) was added portionwise to a solution of diethyl malonate (11.7 g) in N,N-dimethylformamide (50 ml) and the mixture was stirred for 10 minutes. A solution of 5-bromomethyl-2-methyl-4-phenyloxazole (9.2 g) in N,N-dimethylformamide (20 ml) was added dropwise under ice-cooling. The mixture was stirred under ice-cooling for 30 minutes, diluted with water, and extracted with ethyl ether. The ethyl ether layer was washed with water and dried over anhydrous sodium sulfate. The solvent was then distilled off and the residue was purified by silica gel chromatography [silica gel: 120 g; eluent: hexane-ethyl ether (3:2)] to give an oil (8.0 g) of diethyl 2-(2-methyl-4-phenyl-5-oxazolylmethyl)malonate.

NMR (CDCl₃) δ: 1.22 (6H, t), 2.45 (3H, s), 3.33–3.97 (3H, m), 4.23 (4H, q), 7.20–7.83 (5H, m).

(4) Diethyl 2-(2-methyl-4-phenyl-5-oxazolylmethyl)-malonate (8.0 g) was dissolved in a mixture of acetic acid (50 ml) and 6N hydrochloric acid (20 ml) and the solution was refluxed with stirring for 3 hours. The solvent was then distilled off and the residue was made alkaline with 2N sodium hydroxide and washed with ethyl ether. The alkaline solution was adjusted to pH 2 with concentrated hydrochloric acid to give 2-methyl-4-phenyloxazole-5-propionic acid as crystals, yield 4.85 g (overall yield from the 5-bromomethyl compound=57.5%). Recrystallization from ethanol gave colorless prisms, yield 3.40 g (overall yield from the bromomethyl compound=40.3%), m.p. 156°–157° C.

Elemental analysis: Calcd. for $C_{13}H_{13}NO_3$: C, 67.52; H, 5.67; N, 6.06; Found: C, 67.58; H, 5.66; N, 6.02.

EXAMPLE 2

(1) α,β-Dibromobutyrophenone (30.6 g) and acetamide (47.2 g) were heated on an oil bath at 130°–140° C. for an hour and then poured into ice-water. The mixture was neutralized with sodium hydrogen carbonate and extracted with ethyl acetate. The ethyl acetate layer was washed with water and dried over anhydrous magnesium sulfate. The solvent was then distilled off and the residue was purified by silica gel chromatography [silica gel: 250 g; eluent: hexane-acetone (8:2)] to give 5-(2-acetoxyethyl)-2-methyl-4-phenyloxazole as an oil, yield 16.6 g (67.8%).

NMR (CDCl$_3$) δ: 1.97 (3H, s), 2.45 (3H, s), 3.18 (2H, t), 4.38 (2H, t), 7.27–7.50 (5H, m).

(2) 2N Sodium hydroxide (40 ml) was added to a solution of 5-(2-acetoxyethyl)-2-methyl-4-phenyloxazole (16.6 g) in methanol (40 ml) and the mixture was stirred for 30 minutes, diluted with water and extracted with ethyl acetate. The ethyl acetate layer was washed with water and dried over anhydrous magnesium sulfate. The solvent was then distilled off and the residue wwas purified by silica gel chromatography (silica gel: 190 g, eluent: isopropyl ether) to give an oil of 5-(2-hydroxyethyl)-2-methyl-4-phenyloxazole, yield 11.7 g (84.8%).

NMR (CDCl$_3$) δ: 2.40 (3H, s), 3.07 (2H, t), 3.20 (1H, broad), 3.97 (2H, broad), 7.23–7.80 (5H, m).

(3) N,N-Dimethylformamide (4.0 ml) was added to a solution of 5-(2-hydroxyethyl)-2-methyl-4-phenyloxazole (10.5 g) in chloroform (100 ml) and, under ice-cooling and stirring, thionyl chloride (11.4 ml) was added dropwise. The mixture was refluxed for 30 minutes and the solvent was distilled off. Then, ice water was added and the mixture was neutralized with sodium hydrogen carbonate and extracted with ethyl ether. The ethyl ether layer was washed with water and dried over anhydrous magnesium sulfate. The solvent was distilled off to give an oil of 5-(2-chloroethyl)-2-methyl-4-phenyloxazole, yield 11.0 g (96.5%).

NMR (CDCl$_3$) δ: 2.43 (3H, s), 3.28 (2H, t), 3.62 (2H, t), 7.20–7.80 (5H, m).

(4) A mixture of 5-(2-chloroethyl)-2-methyl-4-phenyloxazole (9.8 g), sodium iodide (9.9 g) and methyl ethyl ketone (150 ml) was refluxed with stirring for 20 hours. The solvent was distilled off and the residue was diluted with water and extracted with ethyl ether. The ethyl ether layer was washed with water and dried over anhydrous magnesium sulfate. The solvent was then distilled off to give an oil of 5-(2-iodoethyl)-2-methyl-4-phenyloxazole, yield 11.5 g (82.9%).

NMR (CDCl$_3$) δ: 2.42 (3H, s), 3.40 (4H, s), 7.27–7.83 (5H, m).

(5) Sodium cyannide (2.16 g) was dissolved in dimethyl sulfoxide (80 ml) and, with stirring, a solution of 5-(2-iodoethyl)-2-methyl-4-phenyloxazole (11.5 g) in dimethyl sulfoxide (20 ml) was added dropwise. The mixture was stirred for 2 hours, followed by addition of ice-water and extraction with ethyl ether. The ether layer was washed with water and dried over anhydrous magnesium sulfate. The solvent was then distilled off and the oily residue was purified by silica gel chromatography [silica gel: 100 g; eluent: hexane-ethyl ether (1:1)] to give an oil of 2-methyl-4-phenyloxazole-5-propionitrile, yield 3.3 g (42.3%).

NMR (CDCl$_3$) δ: 2.48 (3H, s), 2.73 (2H, t), 3.23 (2H, t), 7.30–7.83 (5H, m). IR (Neat): 2240 cm$^{-1}$.

(6) 2-Methyl-4-phenyloxazole-5-propionitrile (0.7 g) was dissolved in a mixture of ethyl alcohol (7 ml) and 2N sodium hydroxide (7 ml) and the solution was refluxed for 3 hours. The reaction mixture was adjusted to pH 2 with hydrochloric acid and diluted with water to give crystals of 2-methyl-4-phenyloxazole-5-propionic acid, yield 0.75 g (98.7%). Recrystallization from ethanol gave colorless prisms, yield 0.50 g (66.6%). The NMR and IR spectra of this product were in complete agreement with those of the compound obtained in Example 1.

EXAMPLE 3

(1) A mixture of α,β-dibromobutyrophenone (30.6 g) and formamide (50 ml) was heated on an oil bath at 120° C.–130° C. for an hour. Then, saturated aqueous sodium hydrogen carbonate was added and the mixture was extracted with ethyl ether. The ethyl ether layer was washed with water and dried over anhydrous magnesium sulfate. The solvent was then distilled off and the oily residue was further distilled under reduced pressure to give an oil of 5-(2-formyloxyethyl)-4-phenyloxazole, yield 12.9 g (59.4%), b.p. 136°–137° C./0.4 mmHg.

NMR (CDCl$_3$) δ: 3.28 (2H, t), 4.52 (2H, t), 7.28–8.00 (5H, m), 7.88 (1H, s), 8.05 (1H, s).

(2) 2N Sodium hydroxide (40 ml) was added to a solution of 5-(2-formyloxyethyl)-4-phenyloxazole (12.9 g) in ethanol (40 ml). The mixture was stirred for 30 minutes, then diluted with water (80 ml) and extracted with ethyl acetate. The ethyl acetate layer was washed with water and dried over anhydrous magnesium sulfate. The solvent was then distilled off to give 10.0 g (97.3%) of 5-(2-hydroxyethyl)-4-phenyloxazole as an oil.

NMR (CDCl$_3$) δ: 3.07 (1H, broad), 3.12 (2H, t), 3.97 (2H, broad; t after addition of D$_2$O), 7.27–8.00 (5H, m), 7.83 (1H, s).

(3) 5-(2-Hydroxyethyl)-4-phenyloxazole (10.0 g) was dissolved in chloroform (100 ml) and N,N-dimethylformamide (4.4 ml) was added. Under ice-cooling and stirring, 12.6 ml of thionyl chloride was added dropwise and the mixture was refluxed for an hour. The solvent was distilled off, followed by addition of saturated aqueous sodium hydrogen carbonate and extraction with ethyl ether. The ethyl ether layer was washed with water and dried over anhydrous magnesium sulfate. The solvent was then distilled off to give an oil (11.0 g) of 5-(2-chloroethyl)-4-phenyloxazole. This product was dissolved in methyl ethyl ketone (150 ml), followed by addition of sodium iodide (13.0 g). The mixture was refluxed under stirring for 24 hours. The resulting precipitate was filtered off and the filtrate was concentrated, followed by addition of water and extraction with ethyl ether. The ethyl ether layer was washed with water and dried over anhydrous magnesium sulfate. The solvent was distilled off to give an oil of 5-(2-iodoethyl)-4-phenyloxazole, yield 14.4 g (83.2%).

NMR (CDCl$_3$) δ: 3.39 (4H, s), 7.15–8.00 (5H, m), 7.75 (1H, s).

(4) Sodium cyannide (1.18 g) was dissolved in dimethyl sulfoxide (40 ml) and, under stirring, a solution of 5-(2-iodoethyl)-4-phenyloxazole (6.0 g) in dimethyl sulfoxide (20 ml) was added dropwise. The mixture was stirred for 2 hours, followed by addition of ice-water and extraction with ethyl acetate. The ethyl acetate layer was washed with water and dried over anhydrous magnesium sulfate. The solvent was then distilled off and the residual crude 4-phenyloxazole-5-propionitrile was dissolved in a mixture of ethanol (40 ml) and 2N sodium hydroxide (40 ml) and the solution was refluxed under stirring for 2 hours. The reaction mixture was concentrated, diluted with water and washed with dichloromethane. The aqueous layer was adjusted to pH 2 with hydrochloric acid and the resulting crystalline precipitate was collected by filtration and recrystallized from ethyl acetate and then from ethanol to give 4- phenyloxazole-5-propionic acid as prisms, yield 0.95 g (21.8%), m.p. 142°–143° C.

Elemental analysis: Calcd. for $C_{12}H_{11}NO_3$: C, 66.35; H, 5.10; N, 6.45; Found: C, 66.20; H, 5.06; N, 6.24.

EXAMPLE 4

Bromine (2.6 ml) was added dropwise to a solution of 3-(4-chlorobenzoyl)propionic acid (10.6 g) in ethyl ether (200 ml) under stirring. The ethyl ether was distilled off to give 3-bromo-3-(4-chlorobenzoyl)propionic acid. Acetamide (30 g) was added thereto, and the mixture was heated with stirring on an oil bath at 140° C. for an hour. Water was added and the mixture was extracted with ethyl acetate. The ethyl acetate layer was washed with water and dried over anhydrous magnesium sulfate. The solvent was then distilled off and the resulting crystalline precipitate was collected by filtration and washed with ethyl ether to give crystals of 4-(4-chlorophenyl)-2-methyloxazole-5-acetic acid, yield 3.9 g (31.1%). Recrystallization from ethanol gave needles, yield 3.5 g (27.9%), m.p. 215°–216° C.

Elemental analysis: Calcd. for $C_{12}H_{10}ClNO_3$: C, 57.27; H, 4.01; N, 5.57; Found: C, 57.29; H, 4.21; N, 5.37.

EXAMPLE 5

(1) Bromine (5.2 ml) was added dropwise to a solution of 4-chloropropiophenone (16.8 g) in ethyl ether (170 ml) under stirring. The solvent was distilled off to give 4-chloro-α-bromopropiophenone. Acetamide (59.0 g) was added thereto, and the mixture was heated on an oil bath at 130°–140° C. for 40 minutes, diluted with water, neutralized with potassium carbonate and extracted with ethyl ether. The ethyl ether layer was washed with water and dried over anhydrous magnesium sulfate. The solvent was then distilled off and the residue was distilled under reduced pressure to give 4-(4-chlorophenyl)-2,5-dimethyloxazole, yield 17.7 g (85.5%), b.p. 115°–118° C./0.8 mmHg.

NMR (CDCl$_3$) δ: 2.43 (6H, s), 7.43 (2H, d), 7.70 (2H, d).

(2) A solution of 4-(4-chlorophenyl)-2,5-dimethyloxazole (6.21 g), N-bromosuccinimide (5.34 g) and azobisisobutyronitrile (0.25 g) in carbon tetrachloride (90 ml) was refluxed with stirring for 15 minutes, then washed with water, saturated aqueous sodium hydrogen carbonate and water in that order, and dried over anhydrous magnesium sulfate. The solvent was then distilled off and the residue was crystallized from cold ethanol to give 5-bromomethyl-4-(4-chlorophenyl)-2-methyloxazole, yield 6.73 g (78.4%). Recrystallization from ethanol gave needles, melting at 75°–76° C.

NMR (CDCl$_3$) δ: 2.52 (3H, s), 4.67 (2H, s), 7.48 (2H, d), 7.73 (2H, d).

Elemental analysis: Calcd. for $C_{11}H_9BrClNO$: C, 46.11; H, 3.17; N, 4.89; Found: C, 46.43; H, 3.13; N, 5.19.

(3) 60% Sodium hydride in oil (0.6 g) was added portionwise to a solution of diethyl malonate (4.8 g) in N,N-dimethylformamide (50 ml). The mixture was stirred for 10 minutes and a solution of 5-bromomethyl-4-(4-chlorophenyl)-2-methyloxazole (4.30 g) in N,N-dimethylformamide (20 ml) was added dropwise under ice-cooling. The mixture was stirred under ice-cooling for 30 minutes, diluted with water and extracted with ethyl ether. The ethyl ether layer was washed with water and dried over anhydrous magnesium sulfate. The solvent was then distilled off. The residue was dissolved in ethanol (30 ml), 2N sodium hydroxide (50 ml) was added, and the mixture was refluxed for 30 minutes, concentrated and washed with ethyl ether. The aqueous layer was acidified with hydrochloric acid and the precipitate was taken up with ethyl ether. The ethyl ether layer was washed with water and dried over anhydrous magnesium sulfate. The solvent was distilled off and the residue was dissolved in pyridine (30 ml). The solution was refluxed with stirring for an hour and the pyridine was distilled off. To the residue was added water and the mixture was adjusted to pH 2 with hydrochloric acid. The resulting crystalline precipitate was collected by filtration to give 4-(4-chlorophenyl)-2-methyloxazole-5-propionic acid, yield 2.50 g (62.8%). Recrystallization from ethanol gave needles, yield 1.85 g (46.5%), m.p. 211°–212° C.

NMR (DMSO-d$_6$) δ: 2.43 (3H, s), 2.67 (2H, m), 3.17 (2H, m), 7.53 (2H, d), 7.83 (2H, d).

Elemental analysis: Calcd. for $C_{13}H_{12}ClNO_3$: C, 58.77; H, 4.55; N, 5.27; Found: C, 58.56; H, 4.53; N, 5.15.

EXAMPLE 6

Using 2-chloropropiophenone as the starting compound, the procedure of Example 5 was repeated to give the following compounds:

(1) 4-(2-Chlorophenyl)-2,5-dimethyloxazole: oil, yield 73.2%, b.p. 98°–100° C./0.6 mmHg. NMR (CDCl$_3$) δ: 2.27 (3H, s), 2.43 (3H, s), 7.33 (4H, m).

(2) 5-Bromomethyl-4-(2-chlorophenyl)-2-methyloxazole: oil, yield 100%. NMR (CDCl$_3$) δ: 2.55 (3H, s), 4.43 (2H, s), 7.37 (4H, m).

(3) 4-(2-Chlorophenyl)-2-methyloxazole-5-propionic acid: needles (recrystallized from ethanol), yield 37.7%, m.p. 154°–155° C.

Elemental analysis Calcd. for $C_{13}H_{12}ClNO_3$: C, 58.77; H, 4.55; N, 5.27; Found: C, 59.01; H, 4.49; N, 5.13.

EXAMPLE 7

Using 3-chloropropiophenone as the starting compound, the procedure of Example 5-(1) and (2) was repeated to give the following respective compounds (1) and (2):

(1) 4-(3-Chlorophenyl)-2,5-dimethyloxazole: oil, yield 79.7%, b.p. 110°–112° C./0.2 mmHg. NMR (CDCl$_3$) δ: 2.37 (3H, s), 2.45 (3H, s), 7.03–7.80 (4H, m).

(2) 5-Bromomethyl-4-(3-chlorophenyl)-2-methyloxazole: oil, yield 100%.

(3) 60% Sodium hydride in oil (0.47 g) was added portionwise to a solution of diethyl malonate (3.4 g) in N,N-dimethylformamide (20 ml) and under ice-cooling a solution of 5-bromomethyl-4-(3-chlorophenyl)-2-methyloxazole (3 g) in N,N-dimethylformamide (10 ml) was added. The mixture was stirred under ice-cooling for 30 minutes, diluted with water and extracted with ethyl ether. The ethyl ether layer was washed with water and dried over anhydrous magnesium sulfate. The solvent was then distilled off and the residue was dissolved in ethanol (20 ml), followed by addition of 2N sodium hydroxide (20 ml). The mixture was refluxed for 5 minutes, diluted with water and washed with ethyl ether. The aqueous layer was adjusted to pH 2 with hydrochloric acid and extracted with ethyl ether The extract was washed with water and dried over anhydrous magnesium sulfate. The solvent was distilled off and the oily residue (mostly, half-ester) was dissolved in pyridine (20 ml). The solution was refluxed for 2.5 hours. The pyridine was then distilled off and the residue [mostly, ethyl 4-(3-chlorophenyl)-2-methyloxazole-5-propionate] was dissolved in a mixture of ethanol (10 ml) and 2N sodium hydroxide (10 ml). The solution was refluxed for 5 minutes, diluted with water and acidified with hydrochloric acid to give crsytals of 4-(3-chlorophenyl)-2-methyloxazole-5-propionic acid, yield 1.6 g (56.7%), m.p. 159°–160° C.

Elemental analysis: Calcd. for $C_{13}H_{12}ClNO_3$: C, 58.77; H, 4.55; N, 5.27; Found: C, 58.42; H, 4.60; N, 5.00.

EXAMPLE 8

Using 4-trifluoromethylpropiophenone as the starting compound, the procedure of Example 5 was repeated to give the following compounds:

(1) 2,5-Dimethyl-4-(4-trifluoromethylphenyl)oxazole: oil, yield 62.9%. NMR (CDCl₃) δ: 2.43 (3H, s), 2.48 (3H, s), 7.62 (4H, m).

(2) 5-Bromomethyl-2-methyl-4-(4-trifluoromethylphenyl)oxazole: oil. NMR (CDCl₃) δ: 2.52 (3H, s), 4.62 (2H, s), 7.73 (4H, m).

(3) 2-Methyl-4-(4-trifluoromethylphenyl)oxazole-5-propionic acid: needles (recrystallized from ethanol) yield 45.6% [overall yield from the compound obtained in (1)], m.p. 163°–164° C.

Elemental analysis: Calcd. for $C_{14}H_{12}F_3NO_3$: C, 56.19; H, 4.04; N, 4.68; Found: C, 55.93; H, 3.91; N, 4.41.

EXAMPLE 9

Using 3-trifluoromethylpropiophenone as the starting compound, the procedure of Example 5 was repeated to give the following compounds:

(1) 2,5-Dimethyl-4-(3-trifluoromethylphenyl)oxazole: oil, yield 80.9%, b.p. 88°–90° C./0.4 mmHg. NMR (CDCl₃) δ: 2.43 (3H, s), 2.48 (3H, s), 7.33–7.87 (4H, m).

(2) 5-Bromomethyl-2-methyl-4-(3-trifluoromethylphenyl)oxazole: oil, yield 100%. NMR (CDCl₃) δ: 2.48 (3H, s), 4.58 (2H, s), 7.42–8.07 (4H, m).

(3) 2-Methyl-4-(3-trifluoromethylphenyl)oxazole-5-propionic acid: needles (recrystallized from ethanol), yield 30.5%, m.p. 136°–137° C.

Elemental analysis: Calcd. for $C_{14}H_{12}F_3NO_3$: C, 56.19; H, 4.04; N, 4.68; Found: C, 56.14; H, 4.02; N, 4.93.

EXAMPLE 10

(1) 4-Methylthiopropiophenone was brominated in the same manner as Example 5-(1) and then reacted with acetamide to give 2,5-dimethyl-4-(4-methylthiophenyl)oxazole as an oil, yield 68.5%, b.p. 140°–143° C./0.6 mmHg.

NMR (CDCl₃) δ: 2.42 (3H, s), 2.43 (6H, s), 7.20 (2H, d), 7.48 (2H, d).

(2) A mixture of 2,5-dimethyl-4-(4-methylthiophenyl)oxazole (4.38 g), N-bromosuccinimide (3.56 g), azobisisobutyronitrile (0.2 g) and carbon tetrachloride (60 ml) was refluxed with stirring for 15 minutes. The reaction mixture was washed with water, saturated aqueous sodium hydrogen carbonate and water in that order, and dried over anhydrous magnesium sulfate. The solvent was then distilled off and the oily residue was dissolved in N,N-dimethylformamide (20 ml). Under ice-cooling and stirring, the solution was added dropwise to a mixture composed of a solution of diethylmalonate (4.8 g) in N,N-dimethylformamide (60 ml) and 60% sodium hydride in oil (0.96 g). The mixture was stirred under ice-cooling for 30 minutes, diluted with water and extracted with ethyl ether. The ethyl ether layer was washed with water and dried over anhydrous magnesium sulfate. The solvent was distilled off and the residue was refluxed in a mixture of ethanol (20 ml) and 2N sodium hydroxide (20 ml) for an hour, diluted with water and washed with ethyl ether. The aqueous layer was adjusted to pH 2 with hydrochloric acid and extracted with ethyl ehter and the ethyl ether layer was washed with water and dried over anhydrous magnesium sulfate. The solvent was distilled off and the residue was heated in pyridine (40 ml) under reflux for 1.5 hours. The pyridine was then distilled off and water was added. The mixture was adjusted to pH 2 with hydrochloric acid and extracted with ethyl ether. The ethyl ether layer was washed with water and dried over anhydrous magnesium sulfate. The solvent was distilled off. The oily residue which contained 2-methyl-4-(4-methylthiophenyl)oxazole-5-propionic acid was purified by way of esterification. Thus, this oil was dissolved in 10% methanolic hydrogen chloride (40 ml) and the solution was allowed to stand overnight. The solvent was then distilled off, followed by addition of saturated aqueous sodium hydrogen carbonate and extraction with ethyl ether. The ethyl ether layer was washed with water and dried over anhydrous magnesium sulfate. The solvent was distilled off and the residue was purified by silica gel chromatography [silica gel: 50 g, eluent: hexane-ethyl ether (6:4)] to give an oil of methyl 2-methyl-4-(4-methylthiophenyl)oxazole-5-propionate, yield 2.0 g.

(3) Methyl 2-methyl-4-(4-methylthiophenyl)oxazole-5-propionate (2 g) obtained in (2) was heated in a mixture of ethanol (10 ml) and 2N sodium hydroxide (10 ml) on a water bath at 90° C. for 5 minutes, then diluted with water, adjusted to pH 2 with hydrochloric acid and extracted with ethyl ether. The ethyl ether layer was washed with water and dried over anhydrous magnesium sulfate. The solvent was then distilled off and the residue was recrystallised from ethanol to give 2-methyl-4-(4-methylthiophenyl)oxazole-5-propionic acid as plates, yield 1.4 g [overall yield from 2,5-dimethyl-4-(4-methylthiophenyl)oxazole: 25.3%], m.p. 108°–109° C.

Elemental analysis: Calcd. for $C_{14}H_{15}NO_3S$: C, 60.63; H, 5.45; N, 5.05; Found: C, 60.70; H, 5.62; N, 5.28.

EXAMPLE 11

Using 4-fluoropropiophenone as the starting compound, the procedure of Example 5 was repeated to give the following compounds:

(1) 4-(4-Fluorophenyl)-2,5-dimethyloxazole: oil, yield 85.3%, b.p. 88°–90° C./0.5 mmHg. NMR (CDCl₃) δ: 2.43 (6H, s), 6.80–7.83 (4H, m).

(2) 5-Bromomethyl-4-(4-fluorophenyl)-2-methyloxazole: oil, yield 100%. NMR (CDCl₃) δ: 2.50 (3H, s), 4.60 (2H, s), 6.83–7.83 (4H, m).

(3) 4-(4-Fluorophenyl)-2-methyloxazole-5-propionic acid: prisms (recrystallized from ethanol, yield 37.5%, m.p. 166°–167° C.

Elemental analysis: Calcd. for $C_{13}H_{12}FNO_3$: C, 62.65; H, 4.85; N, 5.62; Found: C, 62.26; H, 4.97; N, 5.59.

EXAMPLE 12

(1) Bromine (5.2 ml) was added dropwise to a solution of 4-chloropropiophenone (16.8 g) in ethyl ether (170 ml). The ethyl ether was distilled off, propionamide (58.4 g) was added, and the mixture was heated with stirring on an oil bath at 140°–150° C. for an hour. Water was added and the mixture was neutralized with saturated aqueous sodium hydrogen carbonate and extracted with ethyl ether. The ethyl ether layer was washed with water and dried over anhydrous magnesium sulfate. The solvent was then distilled off to give an oil of 2-ethyl-4-(4-chlorophenyl)-5-methyloxazole, yield 21.5 g (97.3%).

NMR (CDCl$_3$) δ: 1.33 (3H, t), 4.10 (3H, s), 2.73 (2H, 8), 7.23 (2H, d), 7.48 (2H, d).

(2) 2-Ethyl-4-(4-chlorophenyl)-5-methyloxazole (6.6 g) was brominated with N-bromosuccinimide (5.4 g) in carbon tetrachloride (90 ml) in the presence of azobisisobutyronitrile (0.3 g) in the same manner as Example 5-(2). The procedure gave an oil of 5-bromomethyl-4-(4-chlorophenyl)-2-ethyloxazole, yield 100%.

NMR (CDCl$_3$) δ: 1.37 (3H, t), 2.85 (2H, q), 4.60 (2H, s), 7.30 (2H, d), 7.57 (2H, d).

(3) The whole amount of 5-bromomethyl-4-(4-chlorophenyl)-2-ethyloxazole obtained in (2) was worked up in the same manner as Example 5-(3) to give crystals of 4-(4-chlorophenyl)-2-ethyloxazole-5-propionic acid, yield 3.7 g (44.6%). Recrystallization from ethanol gave needles, yield 2.1 g (25.3%), m.p. 160°–161° C.

Elemental analysis Calcd. for C$_{14}$H$_{14}$ClNO$_3$: C, 60.11; H, 5.04; N, 5.01; Found: C, 60.08; H, 5.06; N, 5.04.

EXAMPLE 13

(1) To a mixture of 1-amino-1-phenyl-2-propanone hydrochloride (5.55 g), water (40 ml), ethyl acetate (75 ml) and potassium carbonate (4.55 g) was added dropwise hexanoyl chloride (4.42 g) under ice-cooling and stirring. The mixture was further stirred for an hour with ice-cooling. The ethyl acetate layer was separated, washed with water, diluted hydrochloric acid and water in that order, and dried over anhydrous magnesium sulfate. The solvent was then distilled off and the residue was recrystallized from isopropyl ether to give crystals of 1-hexanoylamino-1-phenyl-2-propanone, yield 5.80 g (78.2%), m.p. 77°–78° C.

Elemental analysis: Calcd. for C$_{15}$H$_{21}$NO$_2$: C, 72.84; H, 8.56; N, 5.66; Found: C, 72.34; N, 8.32; N, 5.46.

(2) Phosphorous oxychloride (5.58 ml) was added to a solution of 1-hexanoylamino-1-phenyl-2-propanone (4.94 g) in toluene (50 ml) and the solution was refluxed with stirring for 40 minutes. The solvent was distilled off and water was added to the residue. The mixture was neutralized with potassium carbonate and extracted with ethyl acetate. The extract was washed with water and dried over anhydrous magnesium sulfate. The solvent was then distilled off and the residue was purified by silica gel chromatography [silice gel: 80 g; eluent: hexane-ethyl ether (4:1)] to give an oil of 5-methyl-2-pentyl-4-phenyloxazole, yield 4.25 g (92.8%).

NMR (CDCl$_3$) δ: 0.95 (3H, t), 1.45 (4H, m), 1.83 (2H, m), 2.52 (3H, s), 2.82 (2H, t), 7.33–7.97 (5H, m).

(3) 5-Methyl-2-pentyl-4-phenyloxazole (4.25 g) was brominated with N-bromosuccinimide (3.4 g) in carbon tetrachloride in the presence of azobisisobutyronitrile (0.2 g). The procedure gave an oil of 5-bromomethyl-2-pentyl-4-phenyloxazole, yield 5.70 g (99.7%).

NMR (CDCl$_3$) δ: 0.97 (3H, t), 1.50 (4H, m), 1.83 (2H, m), 2.80 (2H, t), 4.67 (2H, s), 7.33–8.00 (5H, m).

(4) 5-Bromomethyl-2-pentyl-4-phenyloxazole (1.54 g) was worked up in the same manner as Example 5-(3) to give crystals of 2-pentyl-4-phenyloxazole-5-propionic acid, yield 0.67 g (46.9%). Recrystallization from isopropyl ether gave prisms, yield 0.35 g (24.5%), m.p. 80°–81° C.

Elemental analysis: Calcd. for C$_{17}$H$_{21}$NO$_3$: C, 71.06; H, 7.37; N, 4.87; Found: C, 70.97; H, 7.37; N, 4.91.

EXAMPLE 14

(1) Small pieces of anhydrous aluminum chloride were added to a solution of 3-benzoylpropionic acid (1.78 g) in dichloromethane and bromine (0.51 ml) was added dropwise under stirring. The dichloromethane was distilled off, followed by addition of methanol (20 ml) and concentrated sulfuric acid (0.5 ml). The mixture was allowed to stand at room temperature for 8 hours, then diluted with water and extracted with ethyl ether. The ethyl ether layer was washed with water, saturated aqueous sodium hydrogen carbonate and water in that order, and dried over anhydrous magnesium sulfate. The solvent was then distilled off to give an oil of methyl 3-benzoyl-3-bromopropionate (2.8 g).

NMR (CDCl$_3$) δ: 3.20 (2H, m), 3.60 (3H, s), 5.40 (1H, q), 7.10–7.63 (3H, m), 7.67–8.17 (2H, m).

(2) A mixture of the oil (2.8 g) obtained in (1) and acetamide (5.9 g) was heated with stirring at 130°–140° C. for an hour, diluted with water and extracted with ethyl acetate. The ethyl acetate layer was washed with water, saturated aqueous sodium hydrogen carbonate and water in that order, and dried over anhydrous magnesium sulfate. The solvent was then distilled off and the residue was purified by silica gel chromatography [silica gel: 40 g; eluent: hexane-acetone (9:1)] to give an oil of methyl 2-methyl-4-phenyloxazole-5-acetate (0.54 g; overall yield: 23.3%).

IR (Neat): 1740 cm$^{-1}$. NMR (CDCl$_3$) δ: 2.45 (3H, s), 3.70 (3H, s), 3.78 (2H, s), 7.13–7.67 (5H, m).

(3) 2N Sodium hydroxide (2 ml) was added to a solution of the ester compound (0.54 g) obtained in (2) in ethanol (2 ml) and the mixture was allowed to stand at room temperature for 30 minutes, diluted with water and adjusted to pH 2 with hydrochloric acid, whereupon 2-methyl-4-phenyloxazole-5-acetic acid (0.45 g, 88.2%) separated out. Recrystallization from ethyl ether gave colorless needles, yield 0.3 g (58.8%), m.p. 138°–139° C.

Elemental analysis: Calcd. for C$_{12}$H$_{11}$NO$_3$: C, 66.35; H, 5.10; N, 6.45; Found: C, 66.12; H, 4.99; N, 6.47.

EXAMPLE 15

A mixture of 4-(4-chlorophenyl)-2-methyloxazole-5-propionic acid (10.0 g), methanol (50 ml) and 20% methanolic hydrogen chloride (50 ml) was allowed to stand at room temperature for 2 hours. The solvent was distilled off, followed by addition of water. The mixture was neutralized with potassium carbonate and extracted with ethyl acetate. The ethyl acetate layer was washed with water and dried over anhydrous magnesium sulfate. The solvent was then distilled off and the residue was further distilled under reduced pressure to give crystals of methyl 4-(4-chlorophenyl)-2-methyloxazole-5-propionate, yield 7.7 g (68.8%), b.p. 162° C./0.7 mmHg, m.p. 74°–75° C.

Elemental analysis: Calcd. for C$_{14}$H$_{14}$ClNO$_3$: C, 60.11; H, 5.04; N, 5.01; Found: C, 60.41; H, 4.93; N, 4.98.

EXAMPLE 16

2N Sodium hydroxide (5 ml) was added to a solution of methyl 4-(4-chlorophenyl)-2-methyloxazole-5-propionate (1.4 g) in ethanol (10 ml) and the mixture was allowed to stand at room temperature for 30 minute, diluted with water and adjusted to pH 2 with hydrochloric acid. The resulting crystalline precipitate was collected by filtration and recrystallized from ethanol to give crystals of 4-(4-chlorophenyl)-2-methyloxazole-5- propionic acid, yield 1.17 g (88.6%), m.p. 211°–212° C. The IR and NMR spectra of this compound were in complete agreement with those of the compound obtained in Example 5.

EXAMPLE 17

(1) Bromine (0.51 ml) was added dropwise to a mixture of 4-(4-chlorobenzoyl)butyric acid (2.28 g) in dichloromethane (20 ml) under stirring. The solvent was distilled off and the residue was dissolved in methanol (20 ml). 20% Methanolic hydrogen chloride (15 ml) was added and the mixture was stirred at room temperature for an hour. The solvent was then distilled off and the residue was diluted with water and extracted with ethyl ether. The ethyl ether layer was washed with water and dried over anhydrous magnesium sulfate. Removal of the solvent by distillation gave an oil (3.2 g) of methyl-4-bromo-4-(4-chlorobenzoyl)butyrate.

NMR (CDCl$_3$) δ: 2.53 (4H, m), 3.67 (3H, s), 5.27 (1H, t), 1.37 (2H, d), 7.87 (2H, d).

(2) A mixture of the oil (3.2 g) obtained in (1), acetamide (5.9 g) and potassium carbonate (2.0 g) was heated on a water bath at 130°–140° C. for an hour, diluted with 1N hydrochloric acid, and extracted with ethyl acetate. The ethyl acetate layer was washed with water and dried over anhydrous magnesium sulfate. The solvent was then distilled off and the residue was purified by silica gel chromatography [silica gel: 50 g; eluent: hexane-acetone (9:1)] to give crystals of methyl 4-(4-chlorophenyl)-2-methyloxazole-5-propionate, yield 0.28 g (10.6%), m.p. 74°–75° C. The IR and NMR spectra of this compound were in complete agreement with those of the compound obtained in Example 15.

EXAMPLE 18

(1) 60% Suspension of sodium hydride (1.08 g) in oil was added portionwise to a solution of ethyl 2-chloroacetoacetate (4.4 g) in N,N-dimethylformamide (70 ml) under stirring and ice-cooling. After stirring for 10 minutes, a solution of 5-bromomethyl-4-(4-chlorophenyl)-2-methyloxazole (7.0 g) in N,N-dimethylformamide (10 ml) was added dropwise under ice-cooling to the mixture. The mixture was stirred under ice-cooling for 30 minutes, and then diluted with ice-water and extracted with ethyl acetate. The ethyl acetate layer was washed with water and dried over anhydrous magnesium sulfate. The solvent was then distilled off. The residue was dissolved in ethanol (40 ml), added to an aqueous 2N sodium hydroxide solution (40 ml) under stirring and ice-cooling, and stirred for further 30 minutes. The solution was then diluted with water, washed with ethyl ether and the aqueous layer was adjusted to pH 2 with 2N hydrochloric acid to give crystals of 2-chloro-3-[4-(4-chlorophenyl)-2-methyl-5-oxazolyl]-propionic acid, yield 5.9 g (80.4 %). Recrystallization from methanol gave colorless prisms, m.p. 208°–209° C.

Elemental analysis: Calcd. for C$_{13}$H$_{11}$Cl$_2$NO$_2$: C, 52.02; H, 3.69; N, 4.67; Found: C, 52.12; H, 3.67; N, 4.82.

(2) Zinc dust (0.87 g) was added portionwise under stirring at 80°–90° C. into a suspension of 2-chloro-3-[4-(4-chlorophenyl)-2-methyl-5-oxazolyl]-propionic acid (1.0 g) in acetic acid (10 ml). After heating for 40 minutes, undissolved materials were filtered off and water was added to the filtrate. The resulting crystalline precipitate was collected by filtration to give 4-(4-chlorophenyl)-2-methyloxazole-5-propionic acid, yield 0.83 g (94.3%). Recrystallization from ethanol gave colorless needles, m.p. 211°–212° C. The IR and NMR spectra of this compound were in agreement with those of the compound obtained in Example 5.

EXAMPLE 19

(1) 2-Trifluoromethylpropiophenone was brominated in the same manner as Example 5-(1) and then reacted with acetamide to give 2,5-dimethyl-4-(2-trifluoromethylphenyl)oxazole, yield 74.0%, b.p. 83°–86° C./1.2 mmHg.

NMR (CDCl$_3$) δ: 2.17 (3H, s), 2.43 (3H, s), 7.30–7.77 (4H, m).

(2) 2,5-Dimethyl-4-(2-trifluoromethylphenyl)oxazole was borminated in the same manner as Example 5-(2) to give 5-bromomethyl-2-methyl-4-(2-trifluoromethylphenyl)oxazole as an oil, yield 100%.

NMR (CDCl$_3$) δ: 2.52 (3H, s), 4.37 (2H, s), 7.37–7.83 (4H, m).

(3) 5-Bromomethyl-2-methyl-4-(2-trifluoromethylphenyl)oxazole was reacted with ethyl 2-chloroacetoacetate in the same manner as Example 18-(1) and then hydrolized to give 2-chloro-3-[2-methyl-4-(2-trifluoromethylphenyl)-5-oxazolyl]propionic acid as crystals, yield 56.7%, m.p. 158°–159° C. (recrystallized from iso-propyl ether).

Elemental analysis: Calcd. for C$_{14}$H$_{11}$ClF$_3$NO$_3$: C, 50.39; H, 3.32; N, 4.20; Found: C, 50.56; H, 3.33; N, 4.24.

(4) A mixture of 2-chloro-3-[2-methyl-4-(2-trifluoromethylphenyl)-5-oxazolyl]propionic acid (2.5 g), sodium acetate (0.62 g), 80% ethanol (50 ml) and 10% paladium-carbon (1.0 g) was subjected to catalytic hydrogenation for 8 hours and then the catalyst was filtered off. The filtrate was concentrated, diluted with water and extracted with ethyl acetate. The ethyl acetate layer was washed with water and dried over anhydrous magnesium sulfate. The solvent was distilled off and iso-propyl ether was added to the residue to give crystals of 2-methyl-4-(2-trifluoromethylphenyl)oxazole-5-propionic acid, yield 1.85 g (82.6%). Recrystallization from ether gave colorless prisms. yield 1.45 g (64.7%), m.p. 118°–119° C.

Elemental analysis: Calcd. for C$_{14}$H$_{12}$F$_3$NO$_3$: C, 56.19; H, 4.04; N, 4.68; Found: C, 56.29; H, 3.92; N, 4.67.

PREPARATION EXAMPLE

As an antidiabetic, the compound (I) of this invention can be used in the following exemplary dosage forms and formulations.

| A. Tablet | |
|---|---|
| (1) 4-(4-Chlorophenyl)-2-methyloxazole-5-propionic acid | 30 g |
| (2) Lactose | 70 g |
| (3) Corn starch | 29 g |
| (4) Magnesium stearate | 1 g |
| 1000 tablets | 130 g |

The whole amounts of (1) and (2) are blended with 17 g of (3) corn starch and the mixture is granulated with a paste prepared from 7 g of (3) corn starch. To this granular preparation are further added 5 g of (3) corn starch and the whole amount of (4), and the entire composition is molded on a compression tableting machine to give 1000 tablets 7 mm in diameter and each containing 30 mg of (1).

| B. Capsule | |
| --- | --- |
| (1) 4-(4-Chlorophenyl)-2-methyloxazole-5-propionic acid | 30 g |
| (2) Lactose | 115 g |
| (3) Microcrystalline cellulose | 70 g |

What is claimed is:

1. An oxazole compound of the formula:

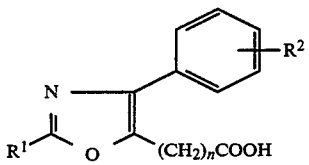

wherein $R^1$ is a straight or branched alkyl group of 1 to 6 carbon atoms, $R^2$ is hydrogen, halogen, trifluoromethyl, a straight or branched alkylthio of 1 to 3 carbon atoms, or a cyclic alkylthio of 3 carbon atoms, and n is 1 or 2; or a pharmaceutically acceptable salt or ester thereof.

2. An oxazole compound as claimed in claim 1, wherein $R^1$ is a straight alkyl of 1 to 5 carbon atoms.

3. An oxazole compound as claimed in claim 1, wherein the oxazole derivative is 2-methyl-4-phenyloxazole-5-propionic acid or its pharmaceutically acceptable salt.

4. An oxazole compound as claimed in claim 1, wherein the oxazole derivative is 4-(4-chlorophenyl)-2-methyloxazole-5-acetic acid or its pharmaceutically acceptable salt.

5. An oxazole compound as claimed in claim 1, wherein the oxazole derivative is 4-(4-chlorophenyl)-2-methyloxazole-5-propionic acid or its pharmaceutically acceptable salt.

6. An oxazole compound as claimed in claim 1, wherein the oxazole derivative is 4-(2-chlorophenyl)-2-methyloxazole-5-propionic acid or its pharmaceutically acceptable salt.

7. An oxazole compound as claimed in claim 1, wherein the oxazole derivative is 4-(3-chlorophenyl)-2-methyloxazole-5-propionic acid or its pharmaceutically acceptable salt.

8. An oxazole compound as claimed in claim 1, wherein the oxazole derivative is 2-methyl-4-(4-trifluoromethylphenyl)oxazole-5-propionic acid or its pharmaceutically acceptable salt.

9. An oxazole compound as claimed in claim 1, wherein the oxazole derivative is 2-methyl-4-(3-trifluoromethylphenyl)oxazole-5-propionic acid or its pharmaceutically acceptable salt.

10. An oxazole compound as claimed in claim 1, wherein the oxazole derivative is 2-methyl-4-(2-trifluoromethylphenyl)oxazole-5-propionic acid or its pharmaceutically acceptable salt.

11. An oxazole compound as claimed in claim 1, wherein the oxazole derivative is 2-methyl-4-(4-methylthiophenyl)oxazole-5-propionic acid or its pharmaceutically acceptable salt.

12. An oxazole compound as claimed in claim 1, wherein the oxazole derivative is 5-(4-fluorophenyl)-2-methyloxazole-5-propionic acid or its pharmaceutically acceptable salt.

13. An oxazole compound as claimed in claim 1, wherein the oxazole derivative is 4-(4-chlorophenyl)-2-ethyloxazole-5-propionic acid or its pharmaceutically acceptable salt.

14. An oxazole compound as claimed in claim 1, wherein the oxazole derivative is 2-n-pentyl-4-phenyloxazole-5-propionic acid or its pharmaceutically acceptable salt.

15. An oxazole compound as claimed in claim 1, wherein the oxazole derivative is 2-methyl-4-phenyloxazole-5-acetic acid methyl ester.

16. An oxazole compound as claimed in claim 1, wherein the oxazole derivative is 2-methyl-4-phenyloxazoleacetic acid or its pharmaceutically acceptable salt.

17. A oxazole compound as claimed in claim 1, wherein the oxazole derivative is 4-(4-chlorophenyl)-2-methyloxazole-5-propionic acid methyl ester.

18. An oxazole compound as claimed in claim 1, wherein the oxazole derivative is 2-methyl-4-(2-trifluoromethylphenyl)oxazole-5-propionic acid or its pharmaceutically acceptable salt.

18. An antidiabetic pharmaceutical composition which comprises an effective amount of a compound represented by the formula:

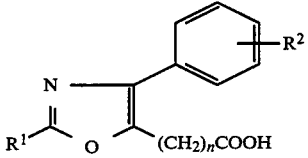

wherein $R^1$ is a straight or branched alkyl group of 1to 6 carbon atoms, $R^2$ is hydrogen, halogen, trifluoromethyl, a straight or branched alkylthio of 1 to 3 carbon atoms, or a cyclic alkylthio of 3 carbon atoms, and n is 1 or 2; or a pharmaceutically acceptable salt or ester thereof, and a pharmaceutically acceptable carrier, excipient or diluent.

19. A composition as claimed in claim 18, wherein $R^1$ is a straight alkyl of 1 to 5 carbon atoms.

* * * * *